United States Patent
Parkhurst et al.

(10) Patent No.: US 7,147,822 B2
(45) Date of Patent: *Dec. 12, 2006

(54) AEROSOL ODOR ELIMINATOR

(75) Inventors: Stephen L. Parkhurst, Cedar Park, TX (US); Morey E. Osborn, Mushogee, OH (US)

(73) Assignee: SL Parkhurst Corporation, Cedar Park, TX (US)

( * ) Notice: Subject to any disclaimer, the term of this patent is extended or adjusted under 35 U.S.C. 154(b) by 37 days.

This patent is subject to a terminal disclaimer.

(21) Appl. No.: 10/614,656

(22) Filed: Jul. 7, 2003

(65) Prior Publication Data

US 2005/0008531 A1  Jan. 13, 2005

(51) Int. Cl.
*A61L 9/00* (2006.01)

(52) U.S. Cl. .................. 422/5; 422/122; 424/76.1
(58) Field of Classification Search .............. 422/5, 422/122; 424/76.1; 4/213.3
See application file for complete search history.

(56) References Cited

U.S. PATENT DOCUMENTS

| | | | |
|---|---|---|---|
| 3,337,992 A | 8/1967 | Tolson | |
| 4,099,047 A | 7/1978 | Kirkland, Jr. | |
| 4,317,242 A | 3/1982 | Stamper | |
| 4,604,110 A | 8/1986 | Frazier | |
| 4,959,207 A | 9/1990 | Ueda et al. | |
| 4,994,245 A | 2/1991 | Murray et al. | |
| 5,253,371 A | 10/1993 | Slawinski | |
| 5,451,346 A | 9/1995 | Amou et al. | |
| 5,454,122 A | 10/1995 | Bergeron | |
| 5,488,741 A | 2/1996 | Hunnicutt | |
| 5,578,563 A | 11/1996 | Trinh et al. | |
| 5,800,806 A | 9/1998 | Yamamoto | |
| 5,896,591 A | 4/1999 | Horan et al. | |
| 5,958,334 A | 9/1999 | Haddon | |
| 5,976,193 A * | 11/1999 | Thomas et al. ............ 8/137 |
| 6,003,157 A | 12/1999 | Bruyere | |
| 6,528,014 B1 | 3/2003 | Parkhurst et al. | |
| 6,635,205 B1 | 10/2003 | Williams et al. | |
| 6,780,403 B1 | 8/2004 | Yamashita et al. | |
| 2001/0028126 A1 | 10/2001 | Williams et al. | |

FOREIGN PATENT DOCUMENTS

| | | |
|---|---|---|
| EP | 0 331 192 A | 6/1989 |
| EP | 1 034 799 A1 | 9/2000 |
| FR | 2622228 | 4/1989 |
| JP | 56115619 A | 9/1981 |

* cited by examiner

*Primary Examiner*—Krisanne Jastrzab
(74) *Attorney, Agent, or Firm*—Vinson & Elkins LLP

(57) ABSTRACT

The invention is a composition, device, system or method for mitigating odors or other contaminants from a target environment. The present invention relates to devices that contain a formulation for removing, in whole or in part, foul odors from the air. In certain embodiments the present invention provides odor-mitigating reagents that are delivered by means of a spray dispenser. The present invention also contemplates applications where the invention can be delivered via a foam or gel dispenser. Certain embodiments of the invention therefore particularly relate to devices such deodorizers, air fresheners and the like.

42 Claims, No Drawings

AEROSOL ODOR ELIMINATOR

BACKGROUND OF THE INVENTION

1. Field of the Invention

The present invention relates to the field of compositions devices, systems and methods for removal, in whole or in part, of undesired odors, pollutants or toxins.

2. Description of Related Art

Since mankind first became aware of the importance of hygiene, the use of antiseptics, sterilization techniques and other similar cares, the issue of malodors, and their potential adverse effects on health and quality of life have been a concern. Bad odors are sometimes an indicator of danger, such as in the case of decay where they can alert one to the possibility of infection or lurking disease. As often as not however, repugnant odors are little more than an unpleasant experience. As such they may not always be indicative of a potential health risk, but rather negatively effect quality of life. Thus, for both nuisance and health reasons, methods have been sought to eliminate or substantially alleviate bad odor experiences wherever they are encountered.

To that end, many devices and techniques have evolved through time to cope with the malodor experience. Such methods or techniques have included masking odors with perfumes, displacing odors with fans or blowers, using activated carbon as malodor absorbers, using electrostatic precipitators, candles, incense and the like. These methods and devices, though somewhat effective in lessening the impact of malodors, do not actually eliminate the malodorous substances themselves.

For example, in the case of activated carbon, malodorants are not changed and may in fact be desorbed as a result of temperature fluctuations or interior carbon particle saturation—thus rendering the method less than optimally effective. This is because the mechanism involved, which entails three separate processes (condensation, Van der Waals attraction and capillary action to the carbon particle interior), leaves the malodorous substances intact. Scrutiny of other traditional methods reveals they too leave the undesired substances intact. In electrostatic precipitation for instance, one sees a process that is fundamentally a flocculation of charged dust particles that are collected at a second stage. However, odor removal with this technique requires adsorption of noxious matter onto the targeted dust particles. This approach is clearly limited by the volatility and adsorbing propensity of the molecules involved. In any case, the odoriferous materials are not converted to less offensive compounds. Similarly, displacement and perfume masking techniques also leave the offending substances unchanged.

Recently, a fundamentally new approach to odor control has been described by the present inventors in U.S. Pat. No. 6,528,014. This "head on" approach uses chemical conversion as the mechanism by which the malodors are rendered innocuous. Certain aspects of the technology described in this patent contrast to the traditional techniques for odor control described above, as it substantially eliminates malodorous substances to benign materials by chemical conversion of the noxious particles or molecules themselves. Additionally, the technology described in U.S. Pat. No. 6,528,014 is shown to be enhanced by the use of substances called "promoters." Appropriate promoters were described as being water-soluble ethylene oxide or propylene oxide derivatives, or mixtures of such.

While the technology of U.S. Pat. No. 6,528,014 is superior over its prior art, it is not as easily adapted as would be desirable in all circumstances to mitigate odors or other contaminants. Thus, there remains a need for compositions, systems and methods that efficiently remove odors or other contaminants from the air and from surfaces.

BRIEF SUMMARY OF THE INVENTION

The present invention includes various embodiments of a composition comprising an odor-mitigating reagent (OMR) that, upon contact with malodorants or other contaminants, can to remove, in whole or in part, such malodorants or contaminants from the area to which the compositions are applied.

In certain embodiments, the OMRs have one or more functional groups capable of chemically neutralizing one or more of the malodorous or other contaminant particles. Thus in certain embodiments the OMRs of the present invention comprise one or more functional groups acting as a Lewis Acid, Lewis Base, oxidizing agent, reducing agent, or other functional group that will chemically neutralize the target particles.

In certain embodiments, the present invention can also include compounds known as promoters to improve the rate of chemical conversion of the malodors or other contaminants by the OMR.

In certain embodiments, the presently disclosed compositions can further comprise additional components that confer characteristics to the composition, as is desired by one skilled in the art, or by the user of the presently disclosed compositions. For example, one can include an antibiotic, a disinfectant, a perfume and/or a foaming agent.

The presently disclosed compositions are dissolved or suspended in a liquid support, and can include a delivery mechanism for applying the compositions to a particular environment.

The liquid support can be any material that serves to allow the OMR to chemically interact with and remove, in whole or in part, the target particles. Similarly, the delivery mechanism can be any mechanism that allows the OMR to chemically interact with target particles after application of the OMR-containing liquid. For example, without limitation, the delivery mechanism can be capable of producing a spray, including aerosol sprays, a foam or a gel.

The presently disclosed compositions are amenable to a variety of useful applications as will be readily apparent to one of skill in the art. Included among these are compositions that, when applied to air, mitigate air-borne odors or contaminants. Such compositions may be used in conjunction with devices such as spray or gel air fresheners or deodorizers (including pump or aerosol spray air fresheners or deodorizers). Alternative embodiments include devices where the compositions are applied to mitigate malodorant or contaminant particles associated with a solid surface. These embodiments may be used in conjunction with devices capable of delivering to a surface a spray, foam or gel containing the compositions. Possible applications for such environments include removal of odors from a human or animal user (e.g. a deodorant) fabric, carpet, upholstery, flooring, bed pans, trash receptacles and the like. Thus the present invention also comprises methods of neutralizing, in whole or in part, malodorants or other contaminants in an environment.

In further embodiments, the compositions of the present invention containing OMRs can be applied to an environment in series. For example, use of the presently disclosed compositions can include application of an OMR with liquid support as described herein where the OMR has one or more functional groups and then sequentially applying an OMR with liquid support as described herein with one or more different or identical functional groups.

Optionally, embodiments of the present invention can further comprise disinfectants, bacteriocidal compounds, fragrances and the like.

DETAILED DESCRIPTION OF THE INVENTION

This invention comprises compositions, devices systems and methods using odor-mitigating reagents (OMRs) that react with malodorants or other contaminants and neutralize, chemically convert or otherwise remove them, in whole or in part, from a surrounding environment. The invention can also include promoters to improve the rate of chemical conversion or neutralization of malodors or other contaminants by the OMRs.

Odor-mitigating compositions, as described, herein, are compositions that are effective to partially or entirely remove from the air or from surfaces, contaminants or other undesired matter. While in preferred embodiments, the odor-mitigating compositions are directed to mitigation of malodorous compounds, the odor-mitigating compositions of the present invention will neutralize any contaminant that will chemically react with the OMRs. Thus the presently disclosed odor-mitigating compositions are effective to mitigate the presence of contaminants such as malodorants, pollutants, toxins, irritants, viruses, microorganisms (such as bacteria, yeast or fungi) and the like.

In general, malodorous materials can be classified into three general chemical types. They are Lewis bases, such as indoles or ammonia, which are encountered in restrooms or hair salons, predominantly neutral compounds such as hydrogen sulfide or mercaptans experienced mostly in bathrooms and Lewis Acids such as butyric acid found in disposable diapers or baby spit-up. In each case there is functionality or a "chemical handle," which can be exploited chemically to eradicate the odor causing substance. In the case of mercaptans, for example, even mild oxidizers can convert them to sulfites, sulfates or other non-volatile, and non-odorous oxidized derivatives. Or, in the case of ammonia, a high molecular weight carboxylic acid can be employed to convert it to a non-volatile salt so it can no longer be detected in the air by primary or secondary human neural receptor sites in the nasal or oral passages. Similarly, other unwanted matter will also have a chemical functional group, or other activity, that can be chemically altered or disabled by one or more of the OMRs of the present invention to remove or neutralize, in whole or in part, that unwanted matter.

"Malodorants" or "malodors" include any objectionable odor-causing chemical agent. "Contaminants" refer to malodorants, pollutants, toxins, irritants, viruses and the like, and microorganisms, such as bacteria, yeast or fungi, wherein said contaminants are capable of reacting with the OMRs of the invention and thus being partially or completely removed from the surrounding or target environment. The term contaminant therefore includes chemical compounds that will react with the OMRs of the present invention (including toxins such as carbon monoxide). While in many portions of the present disclosure the invention is discussed in terms of compositions, devices, systems or methods for mitigating malodorants or malodors, the invention applies equally well to remove any other contaminant that can chemically react with a functional group of one or more OMRs, as taught herein. Accordingly, applications of the presently disclosed compositions, devices, systems and methods to remove contaminants is specifically contemplated herein.

Malodorant or contaminant particles that can be mitigated by the present invention are individual molecules such as ammonia, mercaptans, indoles, pyrroles, hydrogen sulfide, carboxylic acids (e.g. butyric acid), carbon monoxide and the like. Malodorant or contaminant particles that can be mitigated by the present invention can also be larger aggregates of molecules such as bacteria, fungi, spores, viruses and the like.

Odor-mitigating Reagents

The present invention provides OMRs that are capable of reacting with malodorants and other contaminants and sequestering them from their surrounding environment. In certain preferred embodiments, therefore, the presently disclosed compositions comprise one or more OMRs with a functional group such as a Lewis Acid, Lewis Base, oxidizing group (such as a sulfur-labile functional group), a reducing group, or other functional group. OMRs that contain functional groups that are Lewis Bases will react with compounds that are Lewis Acids converting the two compounds into their conjugate salt. The result is that the malodorant becomes permanently bound to the OMR, and therefore incapable of being detected by the user as an unpleasant odor. Conversely, OMRs that contain functional groups that are Lewis Acids will react with compounds that are Lewis Bases to similarly convert those compounds into a bound form that will not be detected by the user. In a similar manner, OMRs having oxidizing agents or hydrosulfur labile functional groups will bind to odor-causing compounds such as mercaptans and hydrogen sulfide. The same mechanism can be used to remove contaminants that will react with an OMR containing a functional group that is a reducing agent. Thus, the principles of the present invention can be readily applied to classes of OMRs that are reducing agents, wherein the reagent can be used to remove any contaminant species that will react with the reducing agent. Other functional groups that can be used to react with malodorous or other unwanted contaminants will be apparent to those of skill in the art.

Due to their incompatibility, it is generally not desirable to mix OMRs that contain Lewis Acids and Lewis Bases. The mixture of these compounds with one another will result in the formation of the conjugate salt of the compounds, thereby effectively reducing or eliminating the effectiveness of the OMR. Similarly, direct mixture of significant quantities of oxidizing reagent with reducing agent will also result in an undesirable reduction in the effectiveness of the OMR. In some embodiments, however, it may be desirable for relatively small quantities of an incompatible compound to be mixed with an excess amount of OMR. This procedure is acceptable as long as a sufficient quantity of unreacted functional groups remain present to chemically react with the contaminants that are to be removed from an environment.

The present invention therefore provides OMRs that contain one or more functional groups that can act as a Lewis Base. Lewis Bases are defined as chemical compounds that can act as an electron pair donor. Examples of non-polymeric Lewis Bases useful in the present invention include, sodium carbonate, Calcite and potassium carbonate. Other appropriate non-polymeric Lewis Bases will be apparent to those of skill in the art.

The present invention also provides for OMRs that contain one or more functional groups that can act as a Lewis Acid. Lewis Acids are defined as chemical compounds that can act as an electron pair acceptor. A Lewis Acid can, for example, convert amines into their conjugate salts. Useful Lewis Acid reagents include ascorbic acid, aspartic acid, phenol, citric acid, maleic acid, oxalic acid and succinic acid. Other appropriate Lewis Acids will be readily apparent to one of skill in the art.

In certain embodiments, the OMR provided by present invention functions as an oxidizing agent or as a hydro-sulfur labile compound. Oxidizing agents and hydro-sulfur labile compounds are especially useful for converting sulfurous compounds such as hydrogen sulfide and mercaptans into non-volatile, non-odorous compounds. Because these compounds are strongly malodorous even at very low levels, chemical capture of these compounds by the OMRs of the present invention is a highly effective means of odor control in many situations. In preferred embodiments the oxidizing agent is a chlorine donor or bleach such as the sodium dichloroisocyanurate, disodium chloroisocyanurate, trichloroisocyanuric acid, dipotassium chloroisocyanurate, dilithium chloroisocyanurate, sodium hypochlorite, calcium hypochlorite, potassium hypochlorite, magnesium hypochlorite, lithium hypochlorite, hypochlorous acid and the like, but other common and exotic oxidizers that can be used in the present invention are listed in U.S. Pat. No. 6,528,014, herein incorporated by reference, and in Tables 1–3, herein.

TABLE 1

Common oxidizers useful for conversion of hydrogen sulfide.

| | |
|---|---|
| 1. | Sodium dichloroisocyanuric acid. |
| 2. | Potassium dichloroisocyanuric acid. |
| 3. | Sodium trichloroisocyanuric. |

TABLE 1-continued

Common oxidizers useful for conversion of hydrogen sulfide.

| | |
|---|---|
| 4. | Potassium trichloroisocyanuric. |
| 5. | Potassium permanganate. |
| 6. | Sodium permanganate. |
| 7. | Sodium hypochlorite in wet solvent. |
| 8. | Potassium hypochlorite in wet solvent. |
| 9. | Hypochlorous acid in wet solvent. |
| 10. | Calcium oxide. |
| 11. | Magnesium oxide. |
| 12. | Chromium trioxide. |
| 13. | Manganese dioxide. |
| 14. | Chromium trioxide-pyidine complex. |
| 15. | Lead tetraacetate. |
| 16. | Barium oxide. |
| 17. | Cadmium oxide. |
| 18. | Lead oxide. |
| 19. | Strontium oxide. |
| 20. | Mercury oxide. |
| 21. | Chromic acid. |
| 22. | Hydrogen peroxide - wet. |
| 23. | Sodium peroxydicarbonate. |
| 24. | Potassium peroxydicarbonate. |
| 25. | Metachloroperbenzoic acid. |
| 26. | Trifluroperacetic acid. |
| 27. | Trichloroperacetic acid. |
| 28. | Perbenzoic acid. |
| 29. | Potassium chromate. |
| 30. | Sodium chromate. |
| 31. | Sodium metaperiodate. |
| 32. | Potassium metaperiodate. |
| 33. | Copper oxide. |
| 34. | Cobalt oxide. |
| 35. | Osmium tetroxide. |
| 36. | Titanium dioxide. |
| 37. | Tungsten oxide. |
| 38. | Diatomic halogens (iodine, chlorine, bromine and fluorine). |

TABLE 2

Exotic oxidizers useful in this invention

| CHEMICAL | GAS # | CROSS-REF |
|---|---|---|
| tert-BUTYLPEROXY NEODECANOATE | [26748-41-4] | |
| tert-BUTYL PEROXYNEOHEPTANOATE | [26748-38-9] | |
| tert-BUTYLPEROXY OCTOATE | [13467-82-8] | tert-BUTYL PEROCTOATE |
| tert-BUTYL PEROXYPHENOXYACETATE | [0-0-0] | |
| 3-tert-BUTYLPEROXY 3-PHENYLPHTHALIDE | [25251-51-8] | |
| tert-BUTYLPEROXY PIVALATE | [927-7-1] | |
| tert-BUTYLPEROXY iso-PROPYL CARBONATE | [2372-21-6] | |
| tert-BUTYLPEROXY STEARYL CARBONATE | [0-0-0] | |
| tert-BUTYLPEROXY o-TOLUATE | [22313-62-8] | |
| tert-BUTYLPEROXY-3,5,5-TRIMETHYLHEXANOATE | [13122-18-4] | |
| O,O-tert-BUTYL-O-iso-PROPYL PEROXYCARBONATE | [0-0-0] | |
| CHLOROPEROXYBENZOIC ACID | [0-0-0] | |
| 3-CHLOROPEROXYBENZOIC ACID | [937-14-4] | m-CHLOROPERBENZOIC ACID |
| 9(11),22-CHOLESTADIEN-246-METHYL-5,8-PEROXY-3b-OL ACETATE | [0-0-0] | |

TABLE 2-continued

Exotic oxidizers useful in this invention

| CHEMICAL | GAS # | CROSS-REF |
|---|---|---|
| 6,9(11),22-CHOLESTATRIEN-246-METHYL-5,8-PEROXY 36-OL ACETATE | [0-0-0] | |
| 6,9,(11),22-CHOLESTATRIEN-246-METHYL-5,8-PEROXY 3b-OL ACETATE | [0-0-0] | |
| COPPER (II) OXYACETATE | [52503-63-6] | |
| COPPER OXYCHLORIDE | [1332-40-7] | |
| COPPER (II) OXYCHLORIDE | [1332-40-7] | COPPER OXYCHLORIDE |
| COPPER OXYCHLORIDE SULFATE | [0-0-0] | |
| TRIMETHYLCYCLOHEXANE | [6731-36-8] | 1,1-BIS(tert-BUTYLPEROXY)-3,3,5-TRIMETHYLCYCLOHEXANE |
| DICETYL PEROXY DICARBONATE | [26322-14-5] | |
| DICYCLOHEXYL PEROXY-DICARBONATE | [1561-49-5] | |
| DI-2-ETHOXYETHYL PEROXYDICARBONATE | [52373-74-7] | |
| DI(2-ETHYLHEXYL)PEROXYDICARBONATE | [16111-62-9] | |
| 2,5-DIHYDROPEROXY-2,5-DIMETHYLHEXANE | [3025-88-5] | |
| 2,4-DIHYDROXY-2-METHYL-4-HYDROPEROXYPENTANE | [0-0-0] | |
| DIMETHOXY iso-PROPYLPEROXYDICARBONATE | [0-0-0] | |
| 2,5-DIMETHYL-2,5-BIS(tert-BUTYLPEROXY)HEXANE | [78-63 7] | 2,5-DIMETHYL-2,5-DI(tert-BUTYLPEROXY)HEXANE |
| 2,5-DIMETHYL-2,5-BIS(tert-BUTYLPEROXY)HEX-3-YNE | [0-0-0] | |
| 2,5-DIMETIYL-2,5-BIS(2-ETHYLHEXOYLPEROXY)HEXANE | [13052-9-0] | 2,5-BIS(2-ETHYLHEXANOYLPEROXY-2,5-DIMETHYLHEXANE |
| 2,5-DIMETHYL-2,5-DI(BENZOYLPEROXY)HEXANE | [2618-77-1] | |
| 2,5-D1METHYL-2,5-DI(tert-BUTYLPEROXY)HEXANE | [78-63-7] | |
| 2,5-DIMETHYL-2,5-Di(tert-BUTYLPEROXY)-3-HEXYNE | [1068-27-5] | 2,5-DIMETHYL-2,5-Di(tert-BUTYLPEROXY)HEXYNE-3 |
| 2,5-DIMETHYL-2,5-DI(tert-BUTYLPEROXY)HEXYNE | [0-0-0] | |
| 2,5-DIMETHYL-2,5-DI(tert-BUTYLPEROXY)HEXYNE-3 | [1068-27-5] | |
| 2,5-DIMETHYL-2,5-DI(2-ETHYLHEXANOYL PEROXY) HEXANE | [13052-9-0] | 2,5-BIS(2-ETHYLHEXANOYLPEROXY 2,5-DIMETHYLHEXANE |
| DI-(3-METHYL-3-METHOXY BUTYL)PEROXYDICARBONATE | [0-0-0] | |
| DIMYRISTYL PEROXYDICARBONATE | [53220-22-7] | |
| DI(PROPYL)PEROXYDICAR-BONATE | [16066-38-9] | |
| Di-iso-PROPYL PEROXYDICARBONATE | [705-64.6] | |
| ETHYL-3,3-BIS(tert-BUTYLPEROXY)BUTYRATE | [55794-20-2] | ETHYL 3,3-DI(tert-BUTYLPEROXY)BUTYRATE |
| ETHYL 3,3-DI(tert-BUTYLPEROXY)BUTYRATE | [55794-20-2] | |
| 2-ETHYLHEXYL PEROXYDICARBONATE | [1611-62-9] | |
| HYDROGEN PEROXY-SULFURIC UREA | [0-0-01] | |
| 1-[(1-HYDROPEROXYCYCLOHEXYL)DIOXY]CYCLOHEXANOL1- | [78-18-21 | |
| HYDROPEROXYCYCLOHEXYL-1-HYDROXY CYCLOHEXYL PEROXIDE | [1226258-7] | CYCLOHEXANONE PEROXIDE |
| 13(S)-HYDROPEROXYOCTADECA-9Z,11E-DIENOIC ACID | [33964-75-9] | |
| 13(8)-HYDROPEROXY-9Z,11E,15Z-OCTADECATRIENOIC ACID | [0-0-0] | |

TABLE 2-continued

Exotic oxidizers useful in this invention

| CHEMICAL | GAS # | CROSS-REF |
|---|---|---|
| MAGNESIUM MONOPEROXYPHTHALATE | [84665-66-7] | |
| MAGNESIUM PEROXYPHTHALATE | [78948-87-5] | |
| MAGNESIUM PEROXYPHTHALATE HEXAHYDRATE | [0-0-0] | |
| MONOPEROXYPHTHALIC ACID, MAGNESIUM SALT | [78948-87-51 | |
| MONOPEROXYPHTHALIC ACID MAGNESIUM SALT HEXAHYDRATE | [84665-66-7] | |
| p-NITROPEROXYBENZOIC ACID | [943-39-5] | 4-NITROPERBENZOIC ACID |
| OXOPEROXYMOLYBDENUM (PYRIDINE)HEXAMETHYLPHOSPHORAMIDE | [23319-63-3] | OXOPIPEROXYMOLYBDENUM (PYRIDINE)HEXAMETHYLPHOSPHORAMIDE |
| OXOPIPEROXYMOLYBDENUM (PYRIDINE)HEXAMETHYLPHOSPHORA-MIDE | [23319-63-3] | |
| PEROXYACETIC ACID | [79-21-0] | PERACETIC ACID |
| PEROXYDICARBONATE | [34099-48-4] | |
| PEROXYDISULFURYL FLUORIDE | [13709-32-5] | |
| PEROXYDOL | [0-0-0] | |
| PEROXYKETAL, CYCLIC | [0-0-0] | |
| PEROXYMONOSULFURIC ACID | [0-0-0] | |
| PEROXYNITRITE | [14042-1-4] | |
| PEROXYNITRITE, TETRAMETHYLAMMONIUM SALT | [157167-78-7] | |
| POTASSIUM PEROXYDIPHOSPHATE | [15593-49-4] | |
| POTASSIUM PEROXYDISULFATE | [7727-21-1] | POTASSIUM PERSULFATE |
| POTASSIUM PEROXY-MONOSULFATE | [0-0-0] | |
| iso-PROPYL-sec-BUTYLPEROXYDICARBONATE | [0-0-0] | |
| SODIUM CARBONATE PEROXYHYDRATE | [0-0-0] | |
| SODIUM PEROXYCARBONATE | [4452-58-8] | |
| SODIUM PEROXYDISULFATE | [7775-27-1] | SODIUM PERSULFATE |
| TETRAKIS(PYRIDINE)SILVER (II) PEROXYDISULFATE | [15810-50-1] | |
| TETRAPOTASSIUM PEROXYDIPHOSPHATE | [0-0-0] | |
| 2,4,4-TRIMETHYLPENTYL-2-PEROXYNEODECANOATE | [0-0-0] | |
| 2,4,4-TRIMETHYLPENTYL-2-PEROXYPHENOXYACETATE | [0-0-0] | |
| VINYL TRIS(tert-)BUTYLPEROXY)SILANE | [15188-9-7] | |

TABLE 3

Hydro-sulfur labile functional groups

1. Carboxylic acid anhydrides
2. Olefins
3. Alkynes
4. Carboxylic acid esters
5. Aldehydes
6. Isonitriles
7. Alkyl halides
8. Alpha diketones
9. Acyl halides
10. Diazo ketones
11. Epoxides
12. Isocyanates
13. Isothiocyanates
14. Thiocyanates
15. Vinyl ethers
16. Diazonium salts
17. Alpha-beta unsaturated carbonyls
18. Ketones
19. Alpha-beta unsaturated nitriles
20. Metal hydrides
21. Carbamates In certain embodiments, a reducing agent can function as an OMR. For example, reducing agents such as sodium sulfite, sodium bisulfite, sodium borohydride and the like can be used to control odors associated with urine.

An effective amount of the OMR is that amount necessary to remove, mitigate or neutralize, in whole or in part, an unwanted target malodorant or contaminant. An effective amount of OMR will vary according to the application and according to the number and type of reactive groups present on the OMRs in the liquid carrier that are available to interact with malodorous or otherwise undesirable compounds in the surrounding environment. Methods of determining the amount of OMR required to reduce the presence of an intended target malodorant or contaminant will be readily apparent to those of skill in the art.

Promoters

Another element of certain embodiments of the present invention are compounds called "promoters." "Promoter" for the purposes of the present invention means humectant compounds that, in the presence of OMRs, promote the chemical conversion of malodorants or other contaminants. Promoters therefore are compounds that are semi-liquid and humectant. They can be either non-polymeric or polymeric compounds.

Promoters of the present invention are compounds that have humectant qualities that attract and/or retain water. In certain embodiments the promoters of the present invention form hydrogen bonds with water having bond strength of at least about 1.0 kcal/mole, at least about 1.5 kcal/mole, at least about 2.0 kcal/mole, at least about 2.5 kcal/mole, or at least about 3.0 kcal/mole. In preferred embodiments, the promoters have hydrogen bonding strengths of 1.5 to 3.5 kcal/mole, and in highly preferred embodiments, 2.0 to 3.0 kcal/mole. Ethylene oxide and propylene oxide derivatives have previously been identified as effective promoters including, for example, polyethylene glycol, polypropylene glycol, nonionic surfactants such as glucan P-20 (Amerchol), ethoxylates such as Tergitol® 9.5 (Union Carbide), Alfonic® Nonionic (Vista Chemical Co.), JL 80X nonionic (Huntsman), cetyl-range ethoxylated nonionics, lauryl-range ethoxylated nonionic surfactants and the like. Other effective promoters include cationic surfactants, carbowax, and the like. Less preferred are anionic surfactants which can be used as the sole promoter or as a supplement to other promoters. Similarly, quaternary ammonium salts can also be used as promoters in this invention, owing to their humectant qualities, and because they have the additional attribute of acting as a disinfectant. In less preferred embodiments of the present invention, soaps can also be used as promoters. Other compounds that have the desired humectant properties and that can be used according to the present disclosure will be readily apparent to those of skill in the art.

The presence of promoters has the beneficial effect of reducing surface tension, which otherwise acts as a partial barrier to absorption of malodors or contaminants found both in air, in liquids and on surfaces. Although not bound by the theory, the inventors believe that promoters act to facilitate faster reaction chemistry between malodor or contaminant molecules and OMRs in liquid carrier than would occur of the promoter were not present due to the reduction in surface tension. Lowering the surface tension of the surface of the OMR-containing composition or device reduces the partial barrier between the OMRs and the target molecules (i.e. malodorants or other contaminants) formed by the surface of the liquid carrier.

Promoters can also exhibit some solvency attributes beyond mere humectancy. Thus, it appears that promoters of the present invention are useful, to some degree, in fostering neutralization (thereby elimination) of odor through promotion of primary odor constituent interaction—i.e. the promoters assist the malodors in neutralizing each other rather than being neutralized any OMRs.

Additional Components of the Compositions

In certain embodiments, the present invention can additionally contain certain additives that improve the manufacturing process or lend other desirable qualities to the final product. For example, in certain embodiments it can be desirable for an odor-mitigating composition or device to also contain compounds with disinfectant or bacteriocidal properties. Examples of disinfectants that can be used in present invention include ethanol, quaternary ammonium salts, biguanides, chelators and other disinfectants and bacteriocidal compounds known to those of skill in the art. Additionally, certain OMRs such as sodium hypochlorite and sodium dichloroisocyanuric acid and act as both an OMR and as a disinfectant.

Further desirable additives may include fragrances and perfumes that do substantially interfere with the function of the OMRs.

In certain embodiments, it may be desirable to add foaming agents that cause the compositions of the present invention to be delivered as a foam. Appropriate foaming agents and mechanisms for their delivery will be readily apparent to those of skill in the art.

In other embodiments, it may be desirable to add gelling agents that cause the compositions of the present invention to be delivered as a gel. Appropriate gelling agents and mechanisms for their delivery will also be readily apparent to those of skill in the art.

Formulation

The composition of this invention in certain preferred embodiments consists of two basic components, promoters and OMRs, in a liquid support.

In general, an odor-fighting composition can be prepared by mixing one or more selected OMRs in the amount of approximately 0.01% to 10% with one or more selected promoters in the amount of 0.01% to 10% suspended or dissolved in a liquid carrier of 50 to 90% water or other carrier substance. (All percentages are calculated by weight.) In preferred embodiments the liquid carrier is generally at least partially aqueous in composition.

A "composition" in the present invention is a liquid carrier comprising one or more of the OMRs of the present invention, with or without promoters or other additives, that when applied by the delivery mechanism to a desired area results in the conversion or neutralization of environmental malodorants or pollutants.

In alternate embodiments, the promoter will be "peaked". Peaked promoters are well-known in the art. Many compounds that are suitable for use as promoters in the present invention come as a mixture of compounds having a range or molecular weights centered around an average molecular weight. In peaked compounds the molecular weights of the molecules in the mixture are more tightly centered (or "peaked") around the average molecular weight, reducing the overall concentration of very high and very low molecular weight compounds. In many embodiments it may be desirable to reduce the concentration of these high or low molecular weight compounds and therefore peaked promoter preparations will be preferred.

In alternate embodiments, rather than being solubilized or suspended directly in the liquid carrier the promoter and/or OMR can be adsorbed onto a solid support (such as a powder) held in liquid suspension. The powder is then dispersed with the liquid carrier by means of the dispensing mechanism.

In preferred embodiments, the composition comprising the OMR, and optionally the promoter or other additive, and liquid carrier is delivered by means of a spray mechanism such as a spray dispenser. A "delivery mechanism" in the present invention is a device capable of delivering an OMR in a liquid carrier to an environment containing a malodorant or other contaminant to be neutralized. For example, the delivery mechanism may deliver the OMR as a gel, foam or spray, including aerosol sprays, and the like.

A spray dispenser can be any of the manually activated means for producing a spray of liquid droplets as is known in the art, e.g. trigger-type, pump-type, electrical spray, hydraulic nozzle, sonic nebulizer, high pressure fog nozzle, non-aerosol self-pressurized, and aerosol-type spray means. Automatic activated means can, also be used herein. These type of automatic means are similar to manually activated means with the exception that the propellant is replaced by a compressor. It is preferred that at least about 70%, more preferably, at least about 80%, most preferably at least about 90% of the droplets have a particle size of smaller than about 200 microns.

In certain embodiments wherein the delivery mechanism is an aerosol delivery mechanism, the composition will be held under pressure in a container and will be dispersed as an aerosol. An aerosol dispenser of the present invention comprises a container which can be constructed of any of the conventional materials employed in fabricating aerosol containers. Aerosol dispensers are generally capable of withstanding internal pressure in the range of from about 5 to about 100 p.s.i.g., more preferably from about 10 to about 60 p.s.i.g. Typically the dispenser is comprises a valve member that permits the OMR-containing composition contained in the dispenser to be dispensed in the form of a spray of very fine, or finely divided, particles or droplets. The aerosol dispenser utilizes a pressurized sealed container from which the composition is dispensed through a special actuator/valve assembly under pressure. The aerosol dispenser is pressurized by incorporating therein a gaseous component generally known as a propellant. Common aerosol propellants, e.g., gaseous hydrocarbons such as isobutane, and mixed halogenated hydrocarbons, are not preferred. Halogenated hydrocarbon propellants such as chlorofluoro hydrocarbons have been alleged to contribute to environmental problems. Preferred propellants are compressed air, nitrogen, inert gases, carbon dioxide, etc. A more complete description of commercially available aerosol-spray dispensers appears in U.S. Pat. No. 3,436,772, Stebbins, issued Apr. 8, 1969; and U.S. Pat. No. 3,600,325, Kaufman et al., issued Aug. 17, 1971; both of said references are specifically incorporated herein by reference.

A broad range of alternate spray mechanisms will be apparent to those of skill in the art. One example is a trigger-spray dispenser. A trigger-spray dispenser typically delivers a discrete amount of the composition by means of a piston or a collapsing bellows that displaces the composition through a nozzle to create a spray of thin liquid. The spray dispenser generally should be capable of providing droplets with a weight average diameter of from 5 to 200 μm preferably from 8 to 100 μm, and most preferably from 10–60 μm.

Sprays, particularly aerosol sprays, are useful in the present invention for the neutralization of air-borne contaminants. Typical applications of such sprays would include, but are not limited to, uses to mitigate household malodors or contaminants, similarly to how air fresheners or deodorizers are currently used.

In alternate embodiments, the composition may be delivered in the form of a foam or gel. Appropriate additives and delivery mechanisms for the production of foams and gels comprising the compositions of the present invention will be apparent to those of skill in the art. Such foam or gel compositions typically would be applied to a surface such as fabric, upholstery, carpeting, flooring, waste receptacles, skin and the like for the neutralization of odors associated with those surfaces.

Due to their inherent incompatibility, Lewis Acids and Lewis Bases generally cannot be usefully mixed in a single reagent package. Similarly, oxidizing agents and reducing agents generally cannot be mixed in a single reagent package. The Lewis Acid and Lewis Base containing OMRs or reagent packages, (or oxidizing agent and reducing agent containing OMRs or reagent packages) can however be applied serially. In these embodiments, for example, the compositions or devices of the present invention can be formulated in pairs meant to be used in series. As an illustration, a typical application would be the provision of pairs of aerosol air fresheners where one of the pair of aerosol sprayers contained a Lewis-Acid OMR and the other a Lewis-Base OMR. One of the pair of sprayers is sprayed by a user to neutralize malodorants or other contaminants in the air. The user then waits for the aerosol spray to dissipate and then sprays the second aerosol sprayer of the pair. The result is the neutralization of a broad range of air-borne malodorants or contaminants.

In certain embodiments it is possible to combine OMRs or other compounds that are ordinarily chemically incompatible due to what is known as "dilution effect" wherein lower concentrations of chemically incompatible compounds may take an extended period of time to react.

In certain embodiments, it will be desirable to select OMRs and promoters that are safe when exposed to human skin or when inhaled (e.g. as when the compositions are aerosolized.) OMRs and promoters that are safe for human or animal contact will be apparent to those of skill in the art.

The compositions, devices and methods of the present invention can produce a significant reduction in the amount of malodorant perceived by users and significant reductions in the quantity of other contaminants found in a particular environment. While smell is highly objective, certain empirical measurements of malodor have been developed, including "panel tests," wherein a panel of testers rate the malodorous qualities of various compositions, or gas-chromatographic "head-space" analyses. Gas-chromatographic analyses may involve gas-chromatography-mass spectral analysis (GC-Mass Spec), or may involve gas-chromatographic analysis alone based on retention time analysis. Such methods are well known to those of skill in the art. Such methods are routinely used to identify and quantify air-borne compounds by introducing a volume of contaminated air into the spectrometer. A significant reduction in malodorant or other contaminants under the present invention may comprise a reduction in malodorant or other contaminant of at least 1%, 2%, 5% 10%, 20%, 30%, 40%, 50%, 60%, 70% 80%, 90%, 95%, 98%, 99% or 100% as measured either by panel tests, by chromatographic "head-space" analysis, or by any other appropriate measurement of malodorant or contaminant concentration available to those of skill in the art.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Aerosol for neutralization of amine odors. A composition is prepared comprising 1 to 10% (by weight) citric acid, 0.01 to 10% ethoxylate (such as DuPont L-588 8 mole ethoxylate) and 50 to 99% water as a liquid carrier. The composition is delivered as an aerosol for the neutralization of amine-based malodorants such as ammonia.

A composition containing 4.0% citric acid, 1.1% ethoxylate and 94.9% water was prepared and delivered as an aerosol. The composition was found to be effective in combating amine odors in air. The preparation of the composition can be aided by premixing a portion of the water with the ethoxylate prior to the addition of the citric acid component.

EXAMPLE 2

Aerosol for neutralization of acid and sulfur odors. A composition is prepared comprising 0.01 to 10% (by weight) sodium dichloroisocyanurate, 0.01 to 11% potassium carbonate, 0.01 to 10% ethoxylate (such as DuPont L-588 8 mole ethoxylate) and 50 to 99% water as a liquid carrier. The composition is delivered as an aerosol for the neutralization of sulfur-containing malodorants and acid-based malodorants.

A composition was prepared comprising 0.25% (by weight) sodium dichloroisocyanurate, 3.01% potassium carbonate, 1.10% ethoxylate (such as DuPont L-588 8 mole ethoxylate) 9.14% of a 5% sodium hypochlorite solution and 86.5% water as a liquid carrier. The composition was effective in combating sulfur and acid odors. Again, the preparation of the composition can be aided by premixing a portion of the water with the ethoxylate prior to the addition of the citric acid component.

EXAMPLE 3

The following composition is a useful buffered solution that was tested and found to be effective for the control of amine odors:
  1.31% potassium carbonate
  6.06% citric acid
  1.11% 8-mole ethoxylate (DuPont L-588)
  91.52% water

EXAMPLE 4

The following composition is useful for the control of amine odors:
  6.06% citric acid
  92.83% water
  1.11% 8-mole ethoxylate (DuPont L-588)

EXAMPLE 5

The following composition is useful for the control of acid or sulfur odors:
  0.25% sodium dichloroisocyanurate
  1.51% potassium carbonate
  9.14% aqueous sodium hypochlorite solution (5%)
  1.10% ethoxylate
  88% water

EXAMPLE 6

The following composition is useful for the control of acid or sulfur odors:
  1.67% sodium dichloroisocyanurate
  5.0% potassium carbonate
  5.0% PEG (polyethylene glycol 6000)
  88.33% water

EXAMPLE 7

The following composition is useful for the control of acid odors:
  6.67% potassium carbonate
  5% ethoxylate
  88.33% water.

All of the compositions, devices, systems and methods disclosed and claimed herein can be made and executed without undue experimentation in light of the present disclosure. While the various aspects of this invention have been described in terms of preferred embodiments, it will be apparent to those of skill in the art that variations may be applied to the compositions, devices, systems and/or methods and in the steps or in the sequence of steps of the methods described herein without departing from the concept, spirit and scope of the invention. More specifically, it will be apparent that certain agents that are chemically or physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A method of removing malodors or contaminants from an environment comprising the steps of
  (a) preparing a composition comprising an odor-mitigating reagent, a promoter and a liquid carrier; and
  (b) contacting the environment with the composition by means of a delivery mechanism, wherein the odor-mitigating reagent is selected from the group consisting of ascorbic acid, aspartic acid, citric acid, maleic acid, oxalic acid, succinic acid, sodium persulfate, potassium persulfate, sodium sulfite, sodium bisulfite and sodium borohydride.

2. The method of claim 1 wherein the environment is air.

3. The method of claim 1 wherein the environment is an inanimate object.

4. The method of claim 1 wherein the environment is a living organism.

5. The method of claim 1 wherein the delivery mechanism is a spray dispenser.

6. The method of claim 5 wherein the spray dispenser is an aerosol dispenser.

7. The method of claim 5 wherein the delivery mechanism is a foam dispenser.

8. The method of claim 1 wherein the delivery mechanism is a gel dispenser.

9. A packaged composition comprising:
   (a) an odor-mitigating reagent,
   (b) a promoter,
   (c) a liquid carrier, and
   (d) a delivery mechanism,
   wherein the odor-mitigating reagent is selected from the group consisting of ascorbic acid, aspartic acid, citric acid, maleic acid, oxalic acid, succinic acid, sodium persulfate, potassium persulfate, sodium sulfite, sodium bisulfite and sodium borohydride.

10. The packaged composition of claim 9 wherein the delivery mechanism is a spray dispenser.

11. The packaged composition of claim 10 wherein the spray dispenser is an aerosol dispenser.

12. The packaged composition of claim 9 wherein the delivery mechanism is a foam dispenser.

13. The packaged composition of claim 9 wherein the delivery mechanism is a gel dispenser.

14. A set of two or more packaged compositions of claim 9 wherein at least one of the packaged compositions contains an odor-mitigating reagent that is chemically incompatible with an odor-mitigating reagent present in another one of the packaged compositions.

15. The set of packaged compositions of claim 14 wherein at least one of the packaged compositions comprises an odor-mitigating reagent that has a functional group capable of acting as a Lewis Acid, and at least one other packaged composition comprises an odor-mitigating reagent that has a functional group capable of acting as a Lewis Base.

16. The set of packaged compositions of claim 14 wherein at least one of the packaged compositions comprises an odor-mitigating reagent that has a functional group capable of acting as an oxidizing agent, and at least one other packaged composition comprises an odor-mitigating reagent that has a functional group capable of acting as a reducing agent.

17. The method of claim 1 wherein the liquid carrier is water.

18. The method of claim 1 wherein the odor-mitigating reagent comprises approximately 0.0 1% to 10% by weight of the composition.

19. The method of claim 1 wherein the odor-mitigating reagent comprises a functional group capable of acting as a Lewis Acid and wherein the odor-mitigating reagent comprises 1% to 10% by weight of the composition.

20. The method of claim 1 wherein the odor-mitigating reagent comprises a functional group capable of acting as a Lewis Acid and wherein the promoter comprises 0.01 to 10% by weight of the composition.

21. The method of claim 1 wherein the odor-mitigating reagent comprises a functional group capable of acting as a Lewis Base and wherein the odor-mitigating reagent comprises approximately 0.01% to 10% by weight of the composition.

22. The method of claim 1 wherein the odor-mitigating reagent comprises a functional group capable of acting as a Lewis Base and wherein the odor-mitigating reagent comprises 1% to 10% by weight of the composition.

23. The method of claim 22 wherein the promoter comprises 0.01 to 10% by weight of the composition.

24. The method of claim 1 wherein the odor-mitigating reagent comprises a functional group capable of acting as an oxidizing agent and wherein the odor-mitigating reagent comprises approximately 0.01% to 10% by weight of the composition.

25. The method of claim 1 wherein the odor-mitigating reagent comprises a functional group capable of acting as an oxidizing agent and wherein the odor-mitigating reagent comprises 1% to 10% by weight of the composition.

26. The method of claim 25 wherein the promoter comprises 0.01 to 10% by weight of the composition.

27. The method of claim 1 wherein the odor-mitigating reagent comprises a functional group capable of acting as a reducing agent and wherein the odor-mitigating reagent comprises approximately 0.01% to 10% by weight of the composition.

28. The method of claim 1 wherein the odor-mitigating reagent comprises a functional group capable of acting as a reducing agent and wherein the odor-mitigating reagent comprises 1% to 10% by weight of the composition.

29. The method of claim 28 wherein the promoter comprises 0.01 to 10% by weight of the composition.

30. The packaged composition of claim 9 wherein the liquid carrier is water.

31. The method of claim 9 wherein the odor-mitigating reagent comprises a functional group capable of acting as a Lewis Acid and wherein the odor-mitigating reagent comprises approximately 0.0 1% to 10% by weight of the composition.

32. The method of claim 31 wherein the odor-mitigating reagent comprises 1% to 10% by weight of the composition.

33. The method of claim 31 wherein the promoter comprises 0.01 to 10% by weight of the composition.

34. The method of claim 9 wherein the odor mitigating reagent comprises a functional group capable of acting as a Lewis Base and wherein the odor-mitigating reagent comprises approximately 0.0 1% to 10% by weight of the composition.

35. The method of claim 34 wherein the odor-mitigating reagent comprises 1% to 10% by weight of the composition.

36. The method of claim 35 wherein the promoter comprises 0.01 to 10% by weight of the composition.

37. The method of claim 9 wherein the odor-mitigating reagent comprises a functional group capable of acting as an oxidizing agent and wherein the odor-mitigating reagent comprises approximately 0.01% to 10% by weight of the composition.

38. The method of claim 37 wherein the odor-mitigating reagent comprises 1% to 10% by weight of the composition.

39. The method of claim 38 wherein the promoter comprises 0.01 to 10% by weight of the composition.

40. The method of claim 9 wherein the odor-mitigating reagent comprises a functional group capable of acting as a reducing agent and wherein the odor-mitigating reagent comprises approximately 0.01% to 10% by weight of the composition.

41. The method of claim 40 wherein the odor-mitigating reagent comprises 1% to 10% by weight of the composition.

42. The method of claim 41 wherein the promoter comprises 0.01 to 10% by weight of the composition.

* * * * *